United States Patent
Striker et al.

(10) Patent No.: US 6,187,745 B1
(45) Date of Patent: Feb. 13, 2001

(54) METHOD OF PREVENTING NEPHROTOXICITY CAUSED BY CYCLOSPORINS AND TACROLIMUS

(75) Inventors: Gary E. Striker; Liliane J. Striker, both of Miami; Kenneth H. Kortright, Pembroke Pines, all of FL (US)

(73) Assignees: Baker Norton Pharmaceuticals, Inc., Miami, FL (US); The United States of America as represented by the Department of Health and Human Services, Washington, DC (US)

( * ) Notice: Under 35 U.S.C. 154(b), the term of this patent shall be extended for 0 days.

(21) Appl. No.: 09/168,974

(22) Filed: Oct. 1, 1998

Related U.S. Application Data

(60) Provisional application No. 60/062,947, filed on Oct. 9, 1997.

(51) Int. Cl.$^7$ .................................................. A61K 38/00
(52) U.S. Cl. ................................................ 514/11; 514/54
(58) Field of Search ...................................... 514/9, 11, 54

(56) References Cited

U.S. PATENT DOCUMENTS

| 5,204,329 | 4/1993 | Akerman et al. |
|---|---|---|
| 5,605,938 * | 2/1997 | Roufa et al. .............................. 514/2 |
| 5,643,892 | 7/1997 | Striker et al. |

FOREIGN PATENT DOCUMENTS 0 466 315 A2   1/1992   (EP) .

OTHER PUBLICATIONS

Bennett et al., *Kid Int.*, vol. 50, pp. 1089–1100 (1996).
Debnam et al., *Kid. Int.*, vol. 50, pp. 1101–1109 (1996).
Andoh et al., *Kid Int.*, vol. 50, pp. 1110–1117 (1996).
Pankewycz et al., *Kid Int.*, vol. 50, pp. 1634–1640 (1996).
Peten, *J. Am. Soc. Neph.*, vol. 41, p. 780, 111p (1993).
Floege et al., *Kid. Int.*, vol. 43, pp. 369–380 (1993).
Naparstek et al., *Arth. &Rheum.*, vol. 33, No. 10, pp. 1554–1559 (1990).
Wardle, *J. Int. Med. Res.*, vol. 20, pp. 361–370 (1992).
Nethery et al., *Biochem. Pharm.*, vol. 44, No. 8, pp. 1549–1553 (1992).
Striker et al., Lab. Inv., vol. 64, No. 4., pp. 446–456 (1991).
Pesce et al., *Lab. Inv.*, vol. 65, No. 5, pp. 601–605 (1991).
Wilke et al., *Cleveland Clin. J. Med.*, pp. 753–754 (Nov./Dec. 1989).
Purkerson et al., *J. Clin. Invest.*, vol. 81, pp. 69–74 (1988).
Herbert et al., *Artery*, vol. 16, No. 1, pp. 1–14 (1988).
Adler, *Am. J. Physiol.*, vol. 255, pp. F781–F786 (1988).
Herbert et al., *Biochem. Pharm.*, vol. 37, No. 22, pp. 4281–4288 (1988).
Andrews, *Chem. Bio. Interactions*, vol. 41, p. 780, 111p (1993).
Fye et al., *Arch Intern. Med.*, vol. 136, pp. 995–999 (1976).
Bone et al., *Kid Int.*, vol. 8, pp. 72–79 (1975).
Zimmerman et al., *Nephron*, vol. 12, pp. 219–230 (1974).
Arieff et al., *Arch. Intern. Med.*, vol. 129, pp. 77–84 (1972).
Freedman et al., *Inv. Urol.*, vol. 7, No. 5, pp. 398–409 (1970).
Kincaid–Smith et al., *The Lancet*, pp. 1360–1364 (1968).
SP54 Package Insert for pentosanpolysulphate sodium, Bene Arzneimittel GmbH.

* cited by examiner

*Primary Examiner*—Zohreh Fay
(74) *Attorney, Agent, or Firm*—Kirschstein, et al.

(57) ABSTRACT

A method of preventing, reducing or reversing nephrotoxicity or renal dysfunction induced by administration of a cyclosporin or tacrolimus to a mammalian patient. The method comprises the co-administration to the patient, either before, together with or after cyclosporin or tacrolimus administration, of a pharmaceutical composition containing an effective amount of pentosan polysulfate (PPS) or a pharmaceutically acceptable salt thereof. The oral route of administration is preferred. The total daily dosage of PPS or PPS salt ranges from about 2 to about 50 mg/kg of patient body weight, or about 140 to about 3,500 mg per day in adult human patients. Also disclosed are a method of providing immunosuppressive therapy to a patient while avoiding cyclosporin or tacrolimus-induced nephrotoxicity, and combination pharmaceutical compositions to be used in such therapy.

42 Claims, 6 Drawing Sheets

FIG. 1B ELMIRON
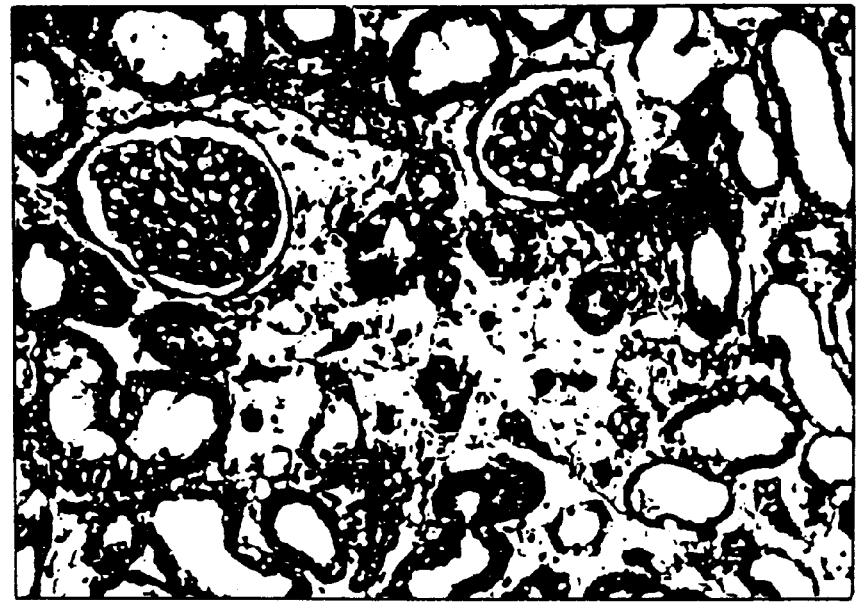
FIG. 1A CONTROL

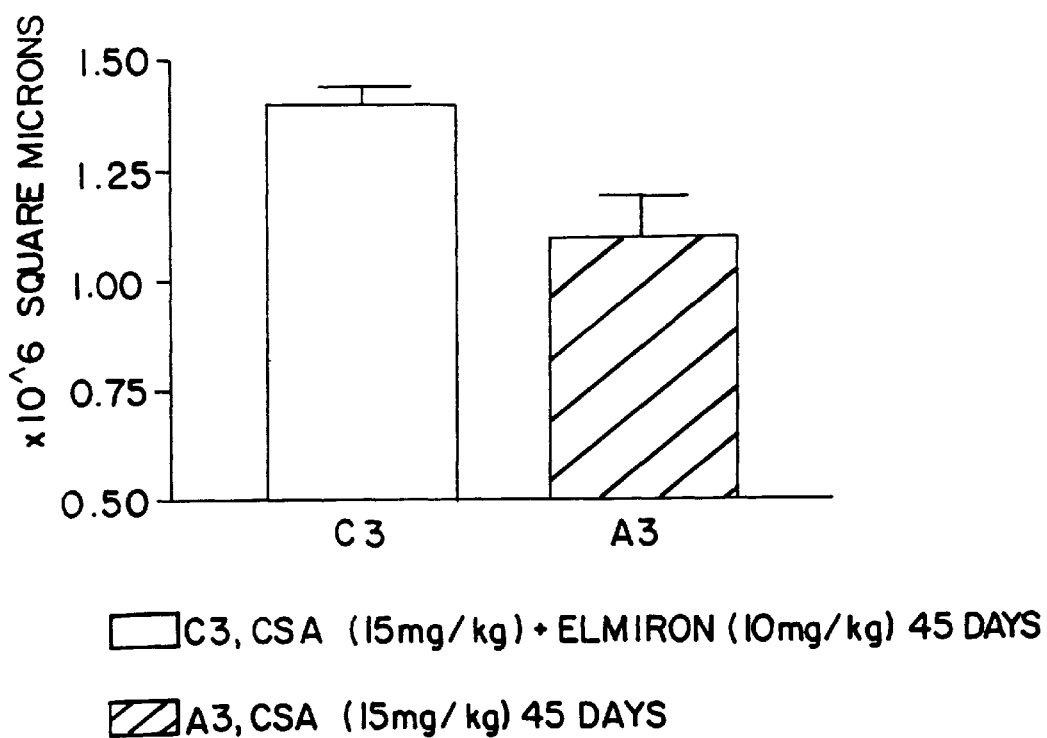

15 DAYS
CyA+E

15 DAYS
CyA

METHOD OF PREVENTING NEPHROTOXICITY CAUSED BY CYCLOSPORINS AND TACROLIMUS

CROSS-REFERENCE TO RELATED APPLICATION

This application claims the priority of Provisional Application Ser. No. 60/062,947, filed Oct. 9, 1997.

BACKGROUND OF THE INVENTION

1. Field of the Invention

The invention relates to methods and pharmaceutical compositions used to prevent kidney toxicity caused by cyclosporin or tacrolimus administration.

2. Description of the Prior Art

Cyclosporins are neutral, lipophilic, cyclic undecapeptides with molecular weights of about 1200. They are used intravenously or orally as immunosuppressants to prolong survival in allogenic transplants involving skin, bone marrow, heart, kidney, pancreas and other organs as well as in the treatment of autoimmune diseases.

One of the principal categories of adverse reactions experienced with cyclosporin therapy is renal dysfunction and toxicity, which creates limitations on the clinical applications of cyclosporins. Indeed, in spite of improved one- and two-year renal allograft survival rates, the average half-life of eight years for a cadaver kidney transplant that is functioning at one year has changed little with the use of cyclosporin-based immunosuppression during the past over 15 years. The adverse effects of cyclosporins, particularly the most commonly used cyclosporin, cyclosporin A (CyA) on long-term kidney structure and function have not been excluded as an important factor in chronic allograft failure syndrome. See Bennett et al., *Kidney Intl.*, 50:1089–1100 (1996).

It has been established that CyA causes a dose-related decrease in renal function in experimental animals and humans which is thought to be due to the drug's effects in producing afferent arteriolar vasoconstriction and, ultimately, decreased glomerular filtration rate. However, these acute hemodynamic effects, which should be largely controllable with precise monitoring and dosing of patients, are apparently not the only adverse consequences of CyA administration for the kidney. Not only patients given CyA therapy to prevent organ transplant rejection, but also patients with autoimmune diseases, have been shown to develop morphologic lesions consisting of areas of striped tubulointerstitial fibrosis, tubular atrophy and afferent arteriolopathy. The hallmark of CyA nephropathy are these vascular lesions, which are not necessarily dose-related and which can be observed in some patients receiving CyA doses as low as 2 to 4 mg/kg. See Bennett et al., ibid.; Pankewycz et al., *Kidney Intl.*, 50:1634–1640 (1996).

No effective technique has been disclosed in the prior art for the chronic administration of CyA and other cyclosporins at therapeutic doses while avoiding the serious consequences of nephrotoxicity. It has been suggested that calcium antagonists may modify the metabolism of CyA, allowing the use of lower doses to achieve adequate immunosuppression. It has also been proposed that dihydropyridine calcium channel blockers may slow interstitial fibrosis in kidney transplant recipients without affecting cyclosporin metabolism. The benefit of these proposed therapies has not been established, however, and there may be adverse effects caused by the chronic administration of calcium antagonists or calcium channel blockers that would outweigh their utility as adjunctive agents to cyclosporins even if they were effective in avoiding kidney damage.

SUMMARY OF THE INVENTION

It is the object of the present invention to provide a method of preventing or substantially reducing the nephrotoxicity caused by the administration of cyclosporins to mammalian patients.

It is another object of the present invention to provide a method as aforesaid which not only halts the disease process but actually reverses that process and causes regression of the scarring lesions.

It is a further object of the invention to provide a method as aforesaid which enables the administration of relatively high, therapeutically effective doses of cyclosporins to patients requiring cyclosporin therapy while avoiding cyclosporin nephrotoxicity and nephropathy.

It is yet another object of the present invention to provide a method as aforesaid utilizing a commercially available pharmaceutical agent which is non-toxic and not likely to provoke serious side effects.

In keeping with these objects and others which will become apparent hereinafter, the invention resides, briefly stated, in a method of preventing, reducing or reversing cyclosporin-induced nephrotoxicity and renal dysfunction in mammalian patients receiving cyclosporin therapy consisting of the administration to such patients of an effective nephrotoxicity-reducing amount of pentosan polysulfate (PPS) or a pharmaceutically acceptable salt thereof. Oral administration of PPS is the preferred mode of administration.

In another aspect, the present invention resides in a method of treating mammalian patients requiring immunosuppressive therapy to prevent allograft rejection or to treat autoimmune diseases through the concomitant administration of an effective immunosuppression-inducing amount of a cyclosporin and an effective nephrotoxicity-reducing amount of PPS of a pharmaceutically acceptable salt thereof. Alternatively, the effective amount of PPS may be administered concomitantly with FK-506 (Fujisawa), also known as tacrolimus, which is used to provide immunosuppression in organ transplant patients, particularly in cases of liver transplants.

BRIEF DESCRIPTION OF THE DRAWINGS

FIG. 1A is a photomicrograph of the kidney of a rat maintained for two weeks on a low sodium diet and then treated with daily injections of CyA for 45 days.

FIG. 1B is a photomicrograph of the kidney of a rat maintained for two weeks on a low sodium diet and then treated with daily injections of CyA and PPS (ELMIRON®) for 45 days.

FIG. 3 is a bar graph reflecting a quantitative comparison of glomerular volume evaluated by morphometric examination of the kidneys of the rats described with respect to FIGS. 1A and 1B, respectively.

DETAILED DESCRIPTION OF THE INVENTION

Figure 2:
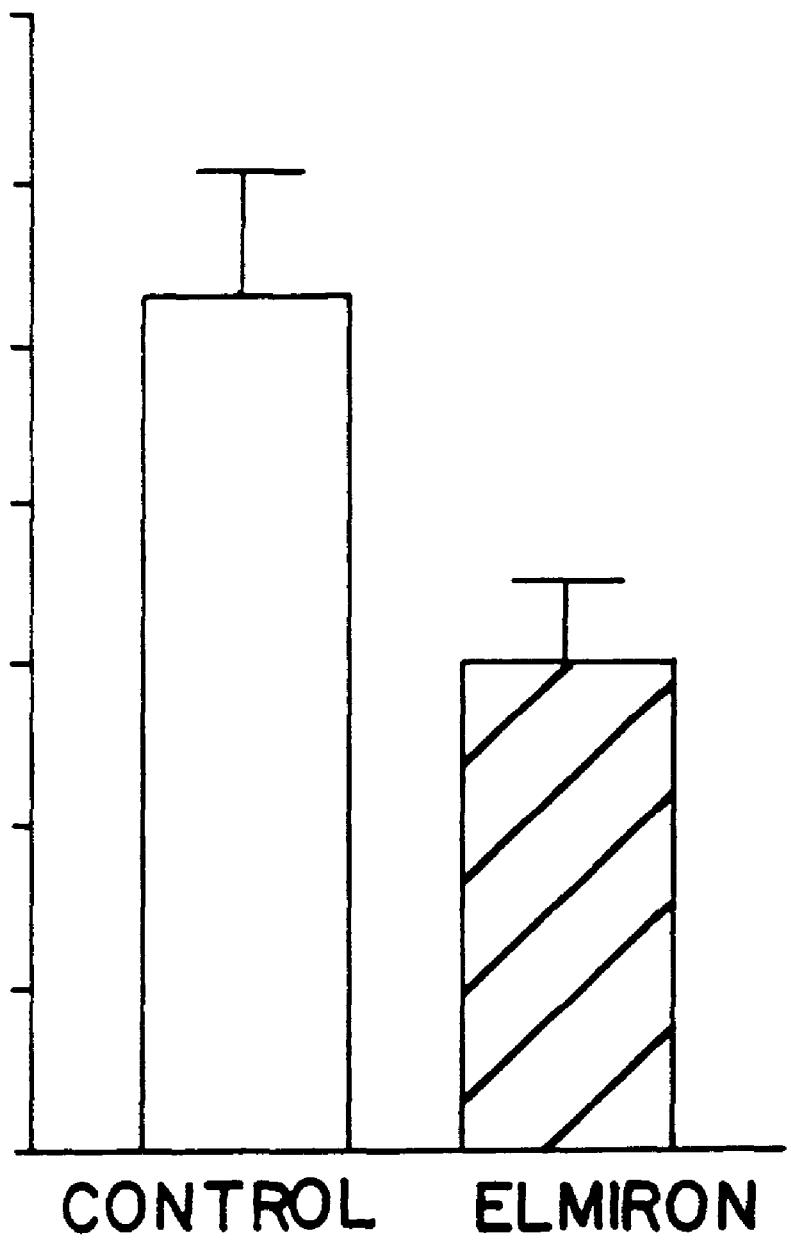
FIG. 2 is a bar graph reflecting a quantitative comparison of the amounts of interstitial fibrosis (expressed in arbitrary units) found on morphometric examination of the kidneys of the rats described with respect to FIGS. 1A and 1B, respectively.

Pentosan polysulfate (PPS) is a highly sulfated, semisynthetic polysaccharide with a molecular weight ranging from about 1,500 to 6,000 Daltons, depending on the mode of isolation. PPS may be in the same general class as heparins and heparinoids, but there are a number of differences in chemical structure, methods of derivation and physico-chemical properties between PPS and heparin. While heparin is usually isolated from mammalian tissues such as beef and pork muscles, liver and intestines, PPS is a semisynthetic compound whose polysaccharide backbone, xylan, is extracted from the bark of the beech tree or other plant sources and then treated with sulfating agents such as chlorosulfonic acid or sulfuryl trichloride and acid. After sulfation, PPS is usually treated with sodium hydroxide to yield the sodium salt.

The structural formula of PPS is shown below (as the sodium salt):

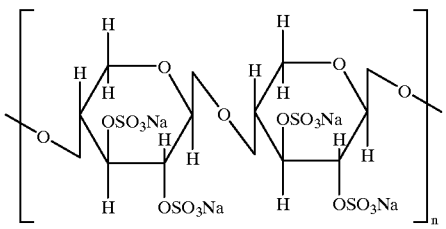

As illustrated, PPS is a sulfated linear polymer of repeating single monomers of (D)-xylose, a 5-carbon pentose sugar in its pyranose ring form. While heparin rotates plane polarized light in a dextrorotatory direction, PPS rotates light in a levorotatory direction.

In terms of biological properties, PPS prolongs partial thromboplastin time and has been used to prevent deep venous thrombosis, but it has only about one-fifteenth the anticoagulant potency of heparin (see generally Wardle, *J. Int. Med. Res.*, 20:361–370, 1992). PPS has also been disclosed, inter alia, as useful in the treatment of urinary tract infections and interstitial cystitis (U.S. Pat. No. 5,180,715); in combination with an angiostatic steroid, in arresting angiogenesis and capillary, cell or membrane leakage (U.S. Pat. No. 4,820,693); and for treatment of chronic, progressive vascular diseases (U.S. Pat. No. 5,643,892), including fibrotic diseases of the kidney such as glomerulosclerosis. Some researchers have demonstrated that PPS inhibits smooth muscle cell proliferation and decreases hyperlipidemia, and on that basis have suggested that PPS might be useful prophylactically in limiting atherosclerotic plaque formation, inhibiting mesangial cell proliferation and preventing collagen formation and glomerulosclerosis (Paul et al., *Thromb. Res.*, 46:793–80, 1987; Wardle, ibid.). However, no one had previously focused on the renal interstitium or small blood vessels (as opposed to inhibition of cell proliferation) or demonstrated that it was feasible to halt and/or reverse acute vascular injury and kidney scarring, i.e., PPS had not been considered in this context. Moreover, none of the prior art suggestions of the possible utility of PPS in scarring diseases was supported by any substantial scientific efficacy data generated in intact animals, but instead were based on in vitro studies of cells isolated from animal tissue(s).

Although there have recently been disclosures of the utility of PPS in the inhibition of fibrosis and scar formation (see, e.g., Roufa et al., U.S. Pat. No. 5,605,938), these teachings deal with the suppression of fibroblast invasion in skin and related tissue areas but not acute or chronic scarring diseases of smooth muscle cells and/or the kidney interstitium which are very different in etiology and pathology.

The present invention relates, in one aspect or embodiment, to a method of preventing, reducing or reversing cyclosporin or tacrolimus-induced nephrotoxicity in mammalian patients receiving cyclosporin or tacrolimus therapy, said method consisting of the administration to such patients of an effective nephrotoxicity-reducing amount of pentosan polysulfate (PPS) or a pharmaceutically acceptable salt thereof. In a second aspect or embodiment, the invention relates to a method of treating patients requiring cyclosporin therapy, e.g., patients requiring immunosuppression to prevent graft rejection or to treat immune diseases, through the concomitant administration of at least one cyclosporin and an effective nephrotoxicity-reducing amount of PPS.

Cyclosporins are currently utilized, or have been disclosed as clinically useful, for the prophylaxis of organ rejection in, for example, kidney, liver, pancreas, bone marrow and heart allogenic transplants; the treatment of autoimmune diseases, e.g., rheumatoid arthritis, systemic lupus erythematosus, multiple sclerosis, myasthenia gravis, Crohn's disease and primary biliary cirrhosis (see, e.g. U.S. Pat. No. 5,204,329); and immunoinflammatory skin diseases such as psoriasis, atopic dermatitis, contact dermatitis, eczematous dermatitis, seborrheic dermatitis, lichen planus, pemphigus, bulus pemphigoid, epidermolysis bullosa, urticaria, angioedemas, vasculitides, erythemas and cutaneous eosiniphilias (see, e.g., U.S. Pat. No. 5,286,730).

In accordance with the invention, a mammalian patient already receiving or about to receive cyclosporin therapy for treatment of any of the aforementioned disease conditions or any other clinical indication is administered an effective nephrotoxicity-reducing amount of PPS or a pharmaceutically acceptable salt thereof. The phrase "an effective nephrotoxicity-reducing amount" as used herein refers to an amount of PPS or a salt thereof incorporated into a pharmaceutical composition which is effective when given one or more times daily for a prescribed period of time (which period may be commenced prior to, concurrently with or after the initiation of cyclosporin therapy) in preventing or substantially diminishing the nephrotoxic effects of the administered cyclosporin.

In human patients, a total daily dosage of PPS or PPS salt of about 2 to about 50 mg/kg, and preferably about 5 to about 30 mg/kg of patient body weight, or about 140 to about 3,500 mg per day in adult patients (and preferably about 350 to about 2,000 mg) administered in one to four divided doses, is effective in achieving the therapeutic goal of preventing, reducing or reversing cyclosporin-induced nephrotoxicity and nephropathy. In smaller mammals, the dosage range may have to be adjusted upward or downward in accordance with body weight, species and the nature of the condition.

The preferred embodiment of the novel method of treatment is the administration to the patient of a pharmaceutical composition comprising an effective amount of PPS or PPS salt and at least one pharmaceutically acceptable inert ingredient. The composition may be in any standard pharmaceutical dosage form, but is preferably an orally administered dosage form.

Dosage forms for oral delivery may include conventional tablets, coated tablets, capsules or caplets, sustained release tablets, capsules or caplets, lozenges, liquids, elixirs or any other oral dosage form known in the pharmaceutical arts.

As pharmaceutically acceptable inert ingredients there are contemplated fillers, binders, solvents, etc. which do not interfere with the desired activity of the PPS. Also, fillers such as clays or siliceous earth may be utilized if desired to adjust the size of the dosage form.

Further ingredients such as excipients and carriers may be necessary to impart the desired physical properties of the dosage form. Such physical properties are, for example, release rate, texture and size. Examples of excipients and carriers useful in oral dosage forms are waxes such as beeswax, castor wax, glycowax and carnauba wax, cellulose compounds such as methylcellulose, ethylcellulose, carboxymethylcellulose, cellulose-acetate phthalate, hydroxypropylcellulose and hydroxypropylmethylcellulose, polyvinyl chloride, polyvinyl pyrrolidone, stearyl alcohol, glycerin monstearate, methacrylate compounds such as polymethacrylate, methyl methacrylate and ethylene glycol dimethacrylate, polyethylene glycol and hydrophilic gums.

In the compositions of the present invention the PPS active ingredient is desirably present in an amount between about 50 and about 300 mg per dosage unit. The exact dosage administered to each patient will be a function of the condition being treated and the physical characteristics of the patient, such as age and body weight.

The active pharmaceutical ingredient can be PPS or a pharmaceutically acceptable salt thereof, e.g., the sodium salt. One preferred oral dosage form for use in the method of the invention is Elmiron® gelatin capsules (Baker Norton Pharmaceuticals, Inc., Miami, Fla.) which contain 100 mg of PPS sodium and, as excipients, microcrystalline cellulose and magnesium stearate.

Although the oral route of administration is preferred, the present method of treatment also comprehends the administration of PPS or a salt thereof via the parenteral, transdermal, transmucosal routes or via any other routes of administration known and conventionally utilized in the medical and pharmaceutical arts. Likewise, the compositions of the invention may include PPS in pharmaceutically acceptable parenteral, transdermal, transmucosal or other conventional vehicles and dosage forms together with suitable inert solvents, excipients and additives. Many examples of such pharmaceutically acceptable vehicles can be found in *Remington's Pharmaceutical Sciences* (17th edition, 1985) and other standard texts. Whatever route of administration or type of pharmaceutical dosage form is used, the daily dosage range for the PPS active ingredient is from about 2 to about 50 mg/kg of patient body weight or about 140 to about 3,500 mg in adult human patients, and preferably about 5 to about 30 mg/kg or about 350 to about 2,000 mg, although dosage amounts towards the lower end of that range would probably be utilized on parenteral administration.

The pharmaceutical compositions used in the method of the invention may include active ingredients other than PPS or a PPS salt, for example, other agents which may be found useful in the prevention of cyclosporin-induced kidney damage or toxicity.

In accordance with the various embodiments of the method of the present invention, the PPS (or PPS salt) containing composition may be administered to the patient before the onset of cyclosporin or tacrolimus therapy (for example, beginning up to several days before), concurrently with the cyclosporin or tacrolimus therapy and/or for a suitable period of time after termination of the cyclosporin or tacrolimus therapy. In a preferred embodiment, at least one dose of PPS or PPS salt is administered to the patient within 24 hrs. prior to, together with or within 24 hrs. subsequent to cyclosporin or tacrolimus administration. The PPS composition may be administered to the patient at the same time as the cyclosporin or tacrolimus composition but in a separate dosage form, or it may be administered to the patient at different times of day than the cyclosporin or tacrolimus-containing composition.

Alternatively, in a further embodiment of the present invention, combination PPS (or PPS salt) and cyclosporin (or tacrolimus) dosage forms may be administered to mammalian patients requiring immunosuppressive therapy. Such combination dosage forms contain an effective immunosuppression-inducing amount of either a cyclosporin or tacrolimus, for example, about 25 to about 200 mg of cyclosporin, preferably CyA. The combination dosage forms also contain an effective nephrotoxicity-reducing amount, e.g., about 50 to about 500 mg, of PPS or a PPS salt. Such dosage forms may be in any suitable form for oral or parenteral delivery or administered as described hereinabove and may contain any pharmaceutically acceptable fillers, binders, solvents, vehicles and other excipients or inert ingredients deemed appropriate by those of skill in the pharmaceutical arts.

The cyclosporin which is currently the most widely used one in clinical applications to provide immunosuppression or to treat autoimmune or immunoinflammatory diseases is CyA, also known as cyclosporine. However, the administration of a PPS composition in accordance with the present invention concomitantly with cyclosporin to prevent nephrotoxicity may be practiced with any cyclosporin, for example, cyclosporins A through Z and derivatives thereof. Moreover, any of cyclosporins A through Z or any other cyclosporin may be employed in a combination dosage form together with PPS or a PPS salt in the novel combination dosage forms of the invention. Also, because the intracellular signalling pathways and renal toxicity profile of FK-506 or tacrolimus resemble those of CyA, it is likely that the toxicity related to tacrolimus administration should also be ameliorated by co-administration of PPS or a PPS salt.

The structures of cyclosporins A through Z (all cyclic undecapeptides) are shown in Table 1.

TABLE 1

Cyclosporins A–Z

| Cyclosporin Cy- | Amino Acids | | | | | | | | | | |
|---|---|---|---|---|---|---|---|---|---|---|---|
| | 1 | 2 | 3 | 4 | 5 | 6 | 7 | 8 | 9 | 10 | 11 |
| CyA | Mebmt | Abu | Sar | MeLeu | Val | MeLeu | Ala | D-Ala | MeLeu | MeLeu | MeVal |
| CyB | Mebmt | Ala | Sar | MeLeu | Val | MeLeu | Ala | D-Ala | MeLeu | MeLeu | MeVal |
| CyC | Mebmt | Thr | Sar | MeLeu | Val | MeLeu | Ala | D-Ala | MeLeu | MeLeu | MeVal |
| CyD | Mebmt | Val | Sar | MeLeu | Val | MeLeu | Ala | D-Ala | MeLeu | MeLeu | MeVal |
| CyE | Mebmt | Abu | Sar | MeLeu | Val | MeLeu | Ala | D-Ala | MeLeu | MeLeu | Val |
| CyF | Desoxy-Mebmt | Abu | Sar | MeLeu | Val | MeLeu | Ala | D-Ala | MeLeu | MeLeu | MeVal |
| CyG | Mebmt | Nva | Sar | MeLeu | Val | MeLeu | Ala | D-Ala | MeLeu | MeLeu | MeVal |
| CyH | Mebmt | Abu | Sar | MeLeu | Val | MeLeu | Ala | D-Ala | MeLeu | MeLeu | D-Mev |
| CyI | Mebmt | Val | Sar | MeLeu | Val | MeLeu | Ala | D-Ala | MeLeu | Leu | MeVal |
| CyK | Desoxy-Mebmt | Val | Sar | MeLeu | Val | MeLeu | Ala | D-Ala | MeLeu | MeLeu | MeVal |
| CyL | Bmt | Abu | Sar | MeLeu | Val | MeLeu | Ala | D-Ala | MeLeu | MeLeu | MeVal |
| CyM | Mebmt | Nva | Sar | MeLeu | Val | MeLeu | Ala | D-Ala | MeLeu | MeLeu | MeVal |
| CyN | Mebmt | Nva | Sar | MeLeu | Val | MeLeu | Ala | D-Ala | MeLeu | Leu | MeVal |
| CyO | MeLeu | Nva | Sar | MeLeu | Val | MeLeu | Ala | D-Ala | MeLeu | MeLeu | MeVal |
| CyP | Bmt | Thr | Sar | MeLeu | Val | MeLeu | Ala | D-Ala | MeLeu | MeLeu | MeVal |
| CyQ | Mebmt | Abu | Sar | Val | Val | MeLeu | Ala | D-Ala | MeLeu | MeLeu | MeVal |
| CyR | Mebmt | Abu | Sar | MeLeu | Val | Leu | Ala | D-Ala | MeLeu | Leu | MeVal |
| CyS | Mebmt | Thr | Sar | Val | Val | MeLeu | Ala | D-Ala | MeLeu | MeLeu | MeVal |
| CyT | Mebmt | Abu | Sar | MeLeu | Val | MeLeu | Ala | D-Ala | MeLeu | Leu | MeVal |
| CyU | Mebmt | Abu | Sar | MeLeu | Val | Leu | Ala | D-Ala | MeLeu | MeLeu | MeVal |
| CyV | Mebmt | Abu | Sar | MeLeu | Val | MeLeu | Ala | D-Ala | MeLeu | MeLeu | MeVal |
| CyW | Mebmt | Thr | Sar | MeLeu | Val | MeLeu | Ala | D-Ala | MeLeu | MeLeu | Val |
| CyX | Mebmt | Nva | Sar | MeLeu | Val | MeLeu | Ala | D-Ala | Leu | MeLeu | MeVal |
| CyY | Mebmt | Nva | Sar | MeLeu | Val | Leu | Ala | D-Ala | MeLeu | MeLeu | MeVal |
| CyZ | MeAminooctyl acid | Abu | Sar | MeLeu | Val | MeLeu | Ala | D-Ala | MeLeu | MeLeu | MeVal |

The following examples demonstrate the efficacy of the novel method in preventing or substantially diminishing and reversing cyclosporin-induced nephrotoxicity, particularly arteriolar necrosis lesions in the kidneys. These examples are merely illustrative and are not intended to set forth materials, compositions or dosage ranges which must be utilized exclusively in order to practice the present invention.

EXAMPLE 1

Two groups of Sprague-Dawley rats were given a low salt diet for two weeks prior to the inception of this experimental study and were kept on that diet for the duration of the study. The first group (control) was then administered 15 mg/kg/day of CyA by injection for a period of 45 days. The second group was administered the same dosage of CyA as the first group but also received daily injections of 10 mg/kg of PPS (ELMIRON®) for the 45-day period. At the end of the study period the animals were sacrificed and their kidneys examined microscopically and by morphometric evaluation.

As reflected in the photomicrographs in FIGS. 1A and 1B, the kidneys of the control group rats exhibited large areas of interstitial fibrosis. There were a small number of inflammatory cells embedded within the fibrotic areas. The kidneys of the rats receiving both CyA and ELMIRON® revealed that most tubules were closely packed together, as in the normal condition, and showed a clear decrease in the amount of fibrosis or cellular infiltrate between the tubules.

The amount of interstitial fibrosis in each of the test groups was assessed quantitatively by morphometric examination of the kidneys. As shown in FIG. 2, there was approximately a 50% reduction in interstitial fibrosis in the ELMIRON® treated rats.

The glomerular size in the kidneys of the rats in the control and ELMIRON® treated groups were measured by image analysis. Fifty glomeruli, sequentially encountered, were evaluated using a standard morphometric technique. As reflected in FIG. 3, the average volume of the glomeruli in the group receiving both CyA and ELMIRON® injections was significantly greater than the glomerular volume in the control group receiving only CyA. This indicated that PPS protected the glomeruli of the rats in the treatment group from ischemic retraction caused by CyA.

EXAMPLE 2

Two groups of Sprague-Dawley rats were given a low salt diet for two weeks prior to the inception of this experimental study and were kept on that diet for the duration of the study. The first group (control) was then administered 15 mg/kg/day of CyA by injection for a period of 15 days. The second group was administered the same dosage of CyA as the first group but also received daily injections of 10 mg/kg of PPS (ELMIRON®) for the 15-day period. At the end of the study period the animals were sacrificed and their kidneys examined microscopically.

Figure 4B:
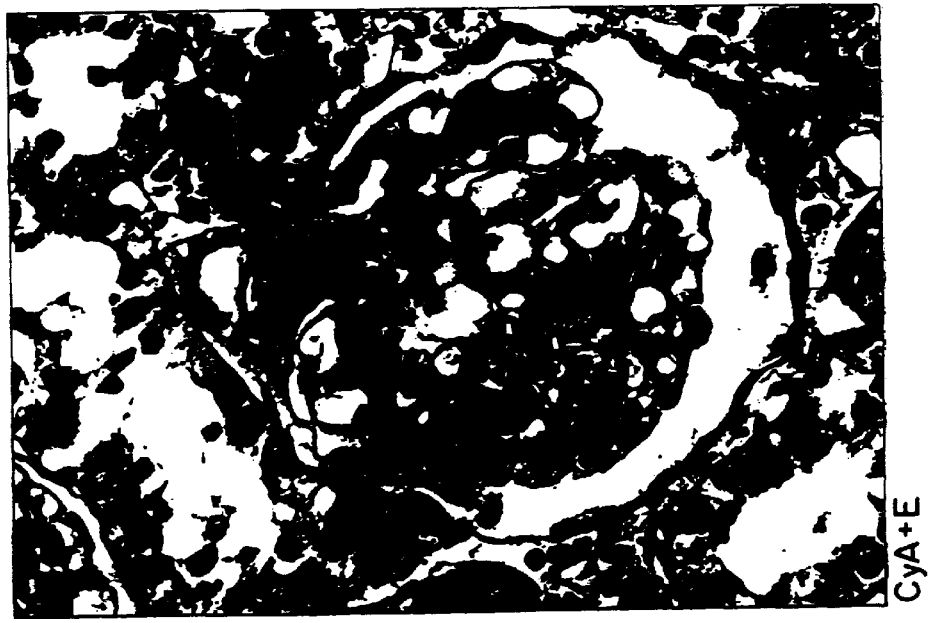
FIG. 4B is a photomicrograph of the kidney of a rat maintained for two weeks on a low sodium diet and then treated with daily injections of CyA and PPS (ELMIRON®) for 15 days.
Figure 4A:
FIG. 4A is a photomicrograph of the kidney of a rat maintained for two weeks on a low sodium diet and then treated with daily injections of CyA for 15 days.

FIGS. 4A and 4B are photomicrographs showing cross-sections of glomeruli from kidneys of a rat from the control group (FIG. 4A) and from the ELMIRON® treated group (FIG. 4B), respectively. In FIG. 4A a small (afferent) arteriole which has "fibrinoid" necrosis involving its entire wall may be seen just to the right of the glomerulus (in the center of the field).

By contrast, there are no lesions in the afferent and efferent arterioles at the glomerular vascular pole shown in FIG. 4B.

Figure 5:
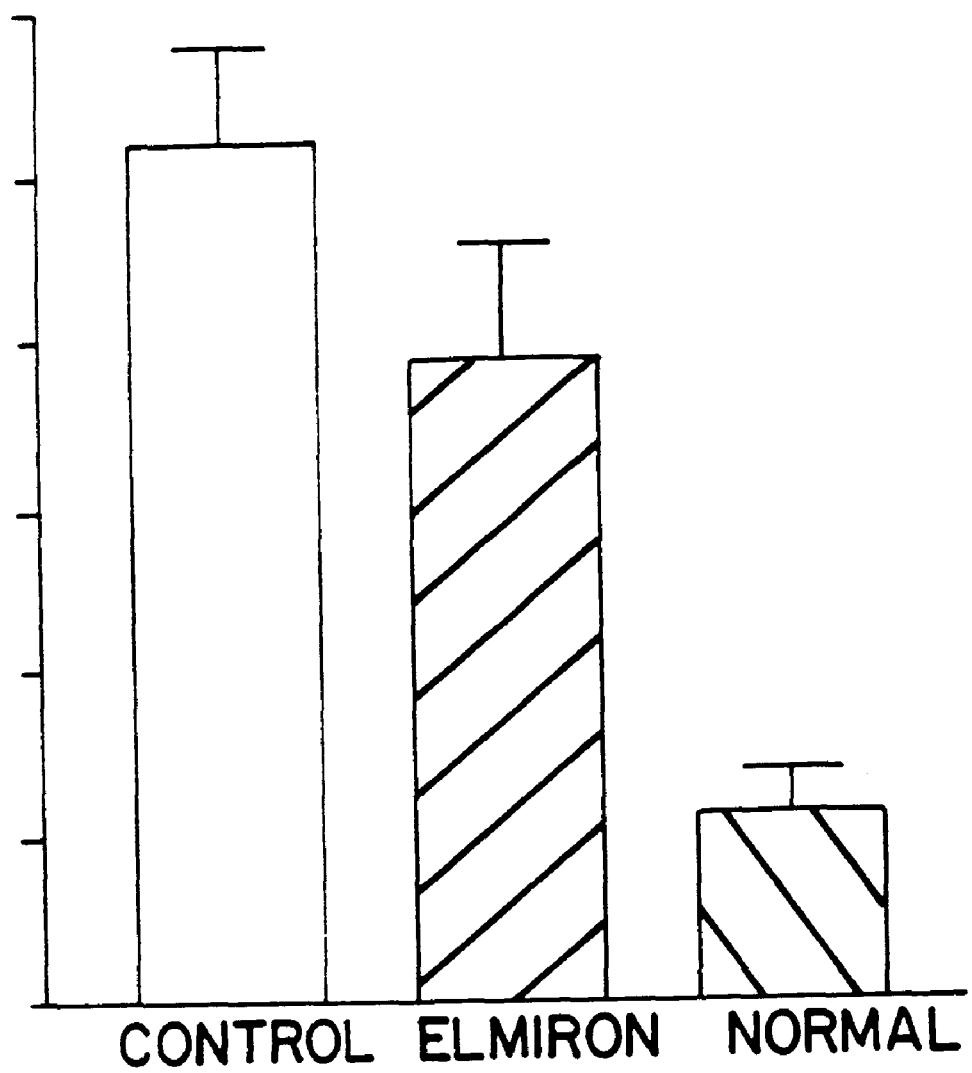
FIG. 5 is a bar graph reflecting a quantitative comparison of the number of fibrinoid lesions assessed in the kidneys of the rats described with respect to FIGS. 4A (control) and 4B (ELMIRON®) and an untreated group of rats, respectively.

The number of "fibrinoid" lesions in afferent arterioles was assessed in the kidney of the control and ELMIRON® treated groups as well as in a group of normal, untreated Sprague-Dawley rats. Fifty sequential vascular pole regions were assessed in each kidney. As reflected in FIG. 5, the number of lesions found in the ELMIRON® treated group was significantly less than in the group of animals receiving CyA alone.

EXAMPLE 3

This study was performed to determine whether PPS had an effect on the gastrointestinal uptake of CyA as reflected in blood CyA levels.

One group of ten Sprague-Dawley rats received CyA (10 mg/kg) in olive oil by gavage. Whole blood levels were taken from each animal at 30 mins., 1 hr., 2 hrs., 3 hrs., 4 hrs., 5 hrs., 6 hrs., 8 hrs., 12 hrs., and 24 hrs. post-CyA administration. CyA levels in the samples were measured by an ELISA method.

Figure 6A:
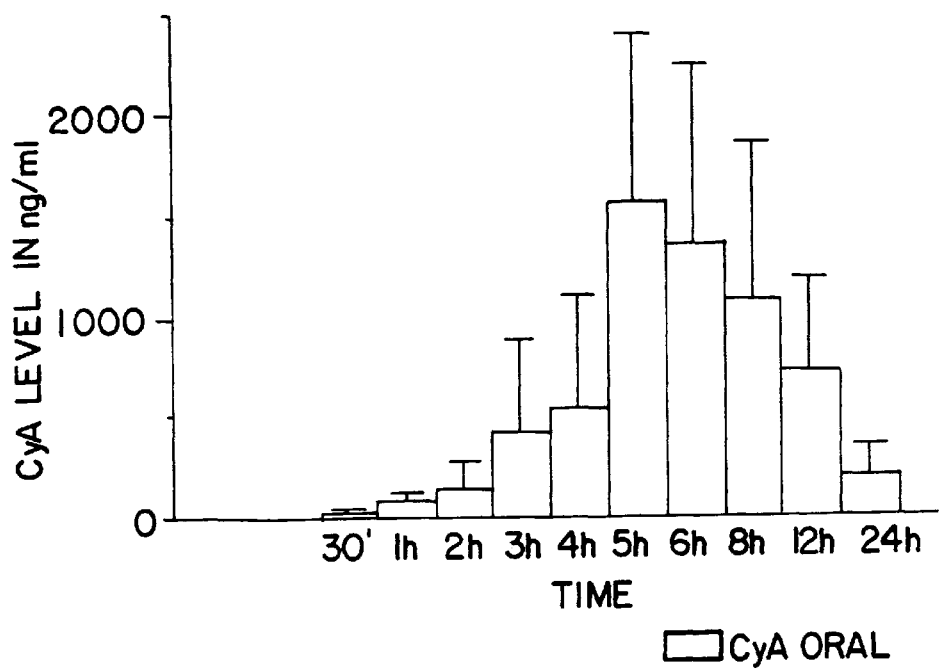
FIG. 6A is a bar graph reflecting the blood levels of CyA determined over a 24-hour period in a group of rats who were administered CyA in olive oil by gavage.

The average CyA levels for this group are reflected in FIG. 6A. Peak blood levels were achieved from 5 to 8 hrs. after administration and returned to near-baseline levels by 24 hrs. There was considerable inter-animal variation, a common finding with this form of CyA.

A second group of 10 Sprague-Dawley rats received CyA (10 mg/kg) in olive oil as well as PPS (ELMIRON®), 5 mg/kg, in water by gavage. Whole blood samples were taken from the animals at the same intervals as in the control group, and CyA levels were measured. The average values for the group at each time interval are reflected in FIG. 6B.

Figure 6B:
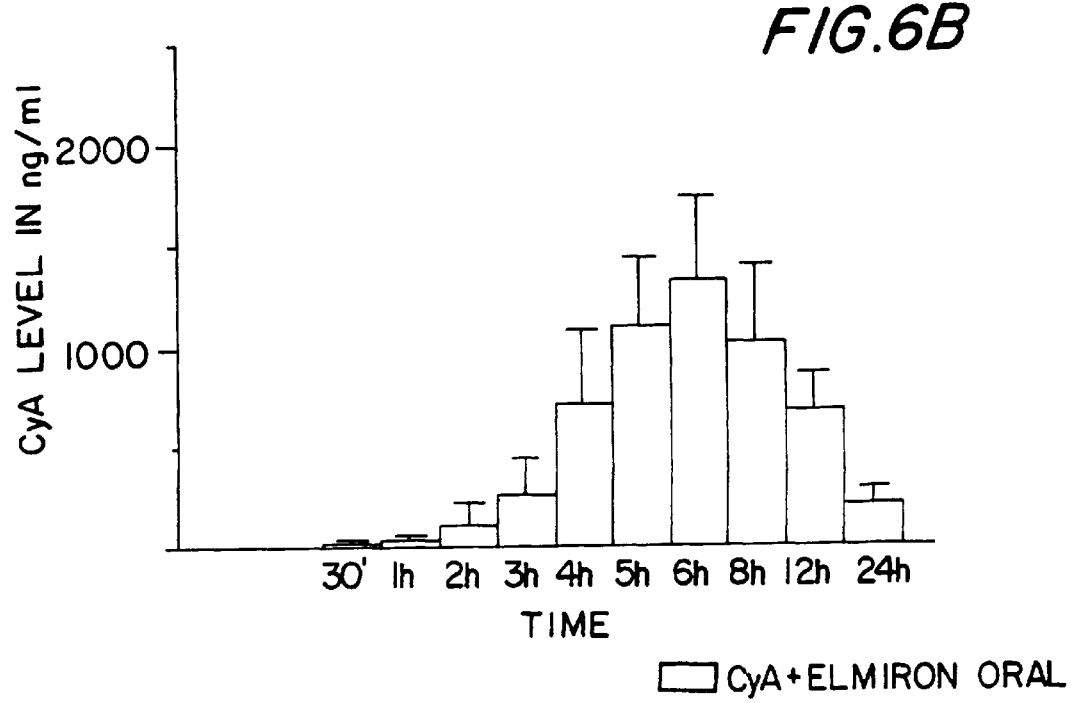
FIG. 6B is a bar graph reflecting the blood levels of CyA determined over a 24-hour period in a group of rats who were administered CyA in olive oil and PPS (ELMIRON®) in water by gavage.

It will be noted that the curve shown in FIG. 6B resembles that seen in FIG. 6A, although inter-animal variation was considerably decreased. These results indicate that the co-administration of oral PPS with oral CyA does not impair the gut absorption of the CyA or decrease the blood levels achieved. Similarly, the concomitant administration of PPS did not affect the plasma disappearance of CyA.

It has thus been shown that there are provided methods and compositions which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the following claims:

1. A method of preventing nephrotoxicity or renal dysfunction involving fibrotic lesions or scarring in the kidney interstitium induced by administration of a cyclosporin or tacrolimus to a mammalian patient, said method comprising co-administration to the patient of a pharmaceutical composition containing an effective nephrotoxicity-reducing amount of pentosan polysulfate (PPS) or a pharmaceutically acceptable salt thereof.

2. A method according to claim 1 wherein said patient is already receiving cyclosporin or tacrolimus therapy.

3. A method according to claim 1 wherein said patient is about to receive cyclosporin or tacrolimus therapy.

4. A method according to claim 1 wherein a dose of said pharmaceutical composition containing PPS or a PPS salt is administered to the patient within 24 hrs. prior to, together with or within 24 hrs. subsequent to cyclosporin or tacrolimus administration.

5. A method according to claim 1 wherein said cyclosporin or tacrolimus is administered to the patient orally or parenterally.

6. A method according to claim 1 wherein said pharmaceutical composition containing PPS or a PPS salt is administered to the patient orally or parenterally.

7. A method according to claim 1 wherein said cyclosporin is selected from the group consisting of cyclosporins A through Z.

8. A method according to claim 7 wherein said cyclosporin is cyclosporin A.

9. A method according to claim 1 wherein a sufficient amount of said pharmaceutical composition is administered to the patient to provide a total daily dose of about 2 to about 50 mg/kg of patient body weight or about 140 to about 3,500 mg of PPS or a pharmaceutically acceptable salt thereof.

10. A method according to claim 9 wherein said daily dose is about 5 to about 30 mg/kg or about 350 to about 2,000 mg.

11. A method according to claim 1 wherein said pharmaceutical composition is an orally administered dosage form.

12. A method according to claim 11 wherein said dosage form is selected from the group consisting of conventional or sustained release tablets, coated tablets, capsules, caplets, lozenges, liquids and elixirs.

13. A method according to claim 11 wherein said dosage form includes at least one pharmaceutically acceptable inert ingredient.

14. A method according to claim 13 wherein said inert ingredient is a filler, binder, solvent, excipient or carrier.

15. A method according to claim 11 wherein said dosage form contains about 50 to about 300 mg per unit of PPS or a pharmaceutically acceptable salt thereof.

16. A method according to claim 14 wherein said pharmaceutical composition is in the form of a gelatin capsule containing PPS sodium, microcrystalline cellulose and magnesium stearate.

17. A method according to claim 1 wherein said pharmaceutical composition is a parenterally administered dosage form.

18. A method according to claim 1 wherein said pharmaceutically acceptable salt is the sodium salt.

19. A method according to claim 1 wherein said patient is a human patient.

20. A method of providing immunosuppressive therapy to a mammalian patient in need of such therapy while preventing or reducing the development of nephrotoxicity or renal dysfunction involving fibrotic lesions or scarring in the kidney interstitium said method comprising co-administration to the patient of an effective immunosuppression-inducing amount of a cyclosporin or tacrolimus and an effective nephrotoxicity-reducing amount of pentosan polysulfate (PPS) or a pharmaceutically acceptable salt thereof.

21. A method according to claim 20 wherein a dose of a pharmaceutical composition containing PPS or a PPS salt is administered to the patient within 24 hrs. prior to, together with or within 24 hrs. subsequent to cyclosporin or tacrolimus administration.

22. A method according to claim 20 wherein said cyclosporin or tacrolimus is administered to the patient orally or parenterally.

23. A method according to claim 21 wherein said pharmaceutical composition containing PPS or a PPS salt is administered to the patient orally or parenterally.

24. A method according to claim 20 wherein said cyclosporin is selected from the group consisting of cyclosporins A through Z.

25. A method according to claim 24 wherein said cyclosporin is cyclosporin A.

26. A method according to claim 21 wherein a sufficient amount of said pharmaceutical composition is administered to the patient to provide a dose of about 2 to about 50 mg/kg of patient body weight or about 140 to about 3,500 mg of PPS or a pharmaceutically acceptable salt thereof.

27. A method according to claim 26 wherein said dose is about 5 to about 30 mg/kg or about 350 to about 2,000 mg.

28. A method according to claim 21 wherein said pharmaceutical composition is an orally administered dosage form.

29. A method according to claim 21 wherein said pharmaceutical composition is a parenterally administered dosage form.

30. A method according to claim 20 wherein said pharmaceutically acceptable salt is the sodium salt.

31. A method according to claim 20 wherein said patient is a human patient.

32. A pharmaceutical composition containing an effective immunosuppression-inducing amount of an immunosuppressive agent selected from the group consisting of a cyclosporin or tacrolimus and an effective nephrotoxicity-reducing amount of pentosan polysulfate (PPS) or a pharmaceutically acceptable salt thereof.

33. A pharmaceutical composition according to claim 32 wherein said immunosuppressive agent is a cyclosporin.

34. A composition according to claim 33 wherein said cyclosporin is selected from the group consisting of cyclosporins A through Z.

35. A composition according to claim 34 which contains about 25 to about 250 mg of cyclosporin and about 50 to about 500 mg of PPS or PPS salt.

36. A composition according to claim 35 wherein said cyclosporin is cyclosporin A.

37. A composition according to claim 32 which is an orally administered dosage form.

38. A composition according to claim 37 wherein said dosage form is selected from the group consisting of conventional or sustained release tablets, coated tablets, capsules, caplets, lozenges, liquids and elixirs.

39. A composition according to claim 37 wherein said dosage form includes at least one pharmaceutically acceptable inert ingredient.

40. A composition according to claim 39 wherein said inert ingredient is a filler, binder, solvent, excipient or carrier.

41. A composition according to claim 32 which is a parenterally administered dosage form.

42. A composition according to claim 32 wherein said pharmaceutically acceptable salt of PPS is the sodium salt.

* * * * *